US008173335B2

(12) United States Patent
Drndic et al.

(10) Patent No.: US 8,173,335 B2
(45) Date of Patent: May 8, 2012

(54) BEAM ABLATION LITHOGRAPHY

(75) Inventors: Marija Drndic, Philadelphia, PA (US); Michael D Fischbein, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 469 days.

(21) Appl. No.: 12/373,607

(22) PCT Filed: Jul. 13, 2007

(86) PCT No.: PCT/US2007/016006
§ 371 (c)(1),
(2), (4) Date: Jul. 9, 2009

(87) PCT Pub. No.: WO2008/010959
PCT Pub. Date: Jan. 24, 2008

(65) Prior Publication Data
US 2010/0009134 A1    Jan. 14, 2010

Related U.S. Application Data

(60) Provisional application No. 60/830,904, filed on Jul. 14, 2006.

(51) Int. Cl.
*G03C 5/00* (2006.01)
(52) U.S. Cl. .......... 430/30; 430/296; 430/311; 430/319; 430/942; 438/584; 250/396 R; 250/492.22
(58) Field of Classification Search .................... 430/30, 430/296, 942, 311, 319; 438/584; 250/396 R, 250/492.22
See application file for complete search history.

(56) References Cited

U.S. PATENT DOCUMENTS

| | | | |
|---|---|---|---|
| 5,393,953 | A | 2/1995 | Itoh et al. |
| 6,261,726 | B1 | 7/2001 | Brooks et al. |
| 6,875,544 | B1 | 4/2005 | Sweatt et al. |
| 7,768,050 | B2 | 8/2010 | Rappe et al. |
| 2004/0079278 | A1 | 4/2004 | Kamins et al. |
| 2006/0141395 | A1 | 6/2006 | Park et al. |

OTHER PUBLICATIONS

Ajayan et al., "Experimental evidence for quasimelting in small particles," Phys. Rev. Lett., Jul. 17, 1989, 63(3), 279-284.
Ajayan et al., "Quasimelting and phases of small particles," Phys. Rev. Lett., Feb. 15, 1988, 60(7), 585-587.
Bezryadin et al., "Quantum suppression of superconductivity in ultrathin nanowires", Nature, Apr. 27, 2000, 404 (6781), 971-974.
Bysakh, "Mechanisms of nano-hole drilling due to nano-probe intense electron beam irradiation on a stainless steel," J. Vac. Sci. Technol B, Nov./Dec. 2004, 22(6), 2620-2627.
Chen et al., Technical Comment, "Comment on Grain Boundary-Mediated Plasticity in Nanocrystalline Nickel," Science, Apr. 15, 2005, vol. 308, 356c.
Fischbein et al., Nanogaps by direct lithography for high resolution imaging and electronic characterization of nanostructures, Appl. Phys. Letts., Feb. 8, 2006, 88, 1-3.
Grant et al., "Transmission electron microscopy 'windows' for nanofabricated structures ", Nanotechnology, Sep. 2004, 15(9), 1175-1181.
Hiraki et al., "Transformation of diamond nanoparticles into onion-like carbon by electron irradiation studied directly inside an ultrahigh-vacuum transmission electron microscope", Appl. Phys. Lett., May 30, 2005, 86(22), 223101.
Iijima et al., "Structural Instability of Ultrafine Particles of Metals," Phys. Rev. Lett., Feb. 10, 1986, 56(6), 616-619.
Kim et al., "Synthesis of gold nanoparticles from gold(I)-alkanethiolate complexes with supramolecular structures through electron beam irradiation in TEM ", J. Am. Chem. Soc., Jul. 20, 2005, 127(28), 9962-9963.
Kizuka et al., "Atomic desorption process in nanometre-scale electron-beam drilling of MgO in high-resolution transmission electron microscopy ", Philos. Mag. Lett., Oct. 1997, 76(4), 289-298.
Kizuka, "Atomic Process of Point Contact in Gold Studied by Time-Resolved High-Resolution Transmission Electron Microscopy ", Phys. Rev. Lett., Nov. 16, 1998, 81(20), 4448-4451.
Kondo et al., "Gold Nanobridge Stabilized by Surface Structure," Phys. Rev. Lett., Nov. 3, 1997, 79(18), 3455-3458.
Krakow et al., "Observation of Quasimelting at the Atomic Level in Au Nanoclusters," Phys. Rev. B, Apr. 15, 1994, 49(15), p. 10 591-10 596.
Lee et al., "In Situ HREM Observation of Crystalline-to-Gas Transition in Nanometer-Sized Ag Particles," Phys. Rev. Lett., PRL 965, Feb. 24, 2006, 075504.
Libera, "Local amorphous thin-film crystallization induced by focused electron-beam irradiation," Appl. Phys. Lett., Jan. 15, 1996, 68(3), 331-333.
Mitsui et al., "Nanoscale Volcanoes: Accretion of Matter at Ion-Sculpted Nanopores", Phys. Rev. Lett., Jan. 23, 2006, 96(3), 036102.
Morkved et al., "Silicon nitride membrane substrates for the investigation of local structure in polymer thin films", Polymer, Jul. 1998, 39(16), 3871-3875.
Niwase et al., "Generation of nanosized grooves and holes on metal surfaces by low-temperature electron irradiation," Philosophical Magazine Letters, Sep. 1996, 74(3), 167-174.
Pandey et al., "Growth and characterization of silicon nitride films for optoelectronics applications", Optical Materials, Nov. 2004, 27(2), 139-146.
Storm et al., "Electron-beam-induced deformations of SiO2 nanostructures," J Appl. Phys., Jul. 1, 2005, 98, 014307.
Storm et al., "Fabrication of solid-state nanopores with single-nanometre precision," Nature Materials, Jul. 13, 2003, 2, 537-540.

(Continued)

*Primary Examiner* — Christopher Young
(74) *Attorney, Agent, or Firm* — Woodcock Washburn LLP

(57) ABSTRACT

Provided are beam ablation lithography methods capable of removing and manipulating material at the nanoscale. Also provided are nanoscale devices, nanogap field effect transistors, nano-wires, nano-crystals and artificial atoms made using the disclosed methods.

37 Claims, 13 Drawing Sheets

OTHER PUBLICATIONS

Takeda et al., "Nanoholes on Silicon Surface Created by Electron Irradiation under Ultrahigh Vacuum Environment," Phys. Rev. Lett., Oct. 20, 1997, 79(16), 2994-2997.

Terrones et al., "Molecular Junctions by Joining Single-Walled Carbon Nanotubes ", Phys. Rev. Lett., Jul. 29, 2002, 89(7), 075505.

Tinkham, "Limits on Superconductivity in Nanoparticles and Nanowires", Journal of Superconductivity, Oct. 2000, 13(5), 801-804.

Valenzuela et al., "Spin-polarized tunneling in room-temperature mesoscopic spin valves", Appl. Phys. Lett., Dec. 13, 2004, 85(24), 5914-5916.

Wang et al., "Effects of annealing and impurities on tensile properties of electrodeposited nanocrystalline Ni," Scripta Materialia, 2004, 51, 1023-1028.

Washburn et al., "Aharonov-Bohm effect in normal metal quantum coherence and transport", Adv. Phys., (no month available) 1986, 35(4), 375-422.

Xu et al., "Nanometer-Scale Modification and Welding of Silicon and Metallic Nanowires with a High-Intensity Electron Beam," Small, Dec. 2005, 1(12), 1221-1229.

Zandbergen et al., "Sculpting Nanoelectrodes with a transmission electron beam for electrical and geometrical characterization of nanoparticles," Nano Letters, Feb. 4, 2005, 5(3), 549-553.

Zgirski et al., "Size Dependent Breakdown of Superconductivity in Ultranarrow Nanowires", Nano Lett., May 6, 2005, 5(6), 1029-1033.

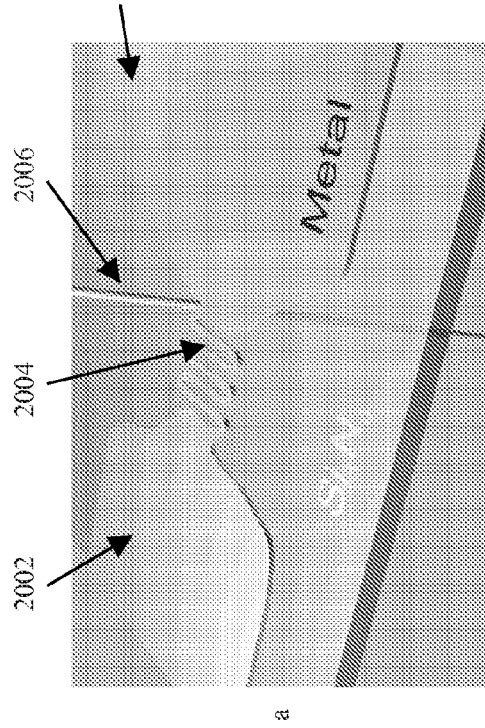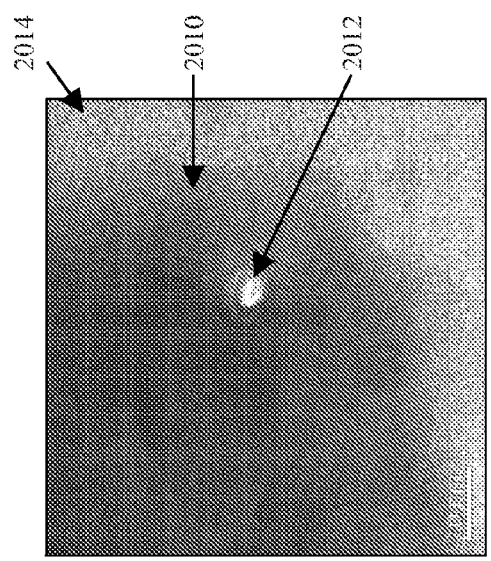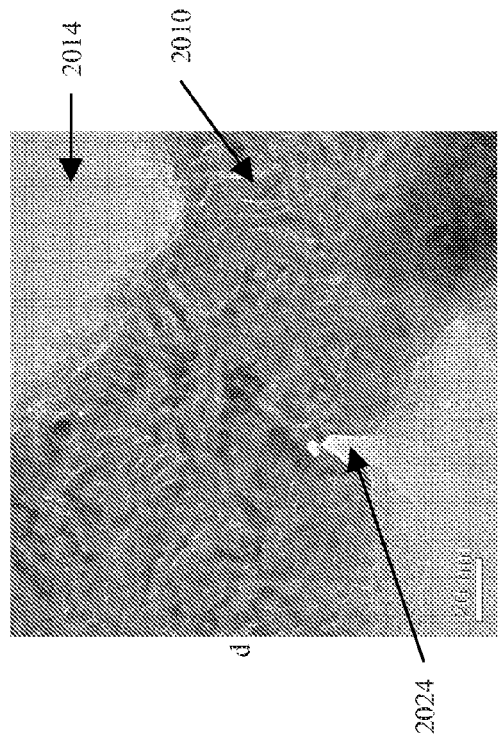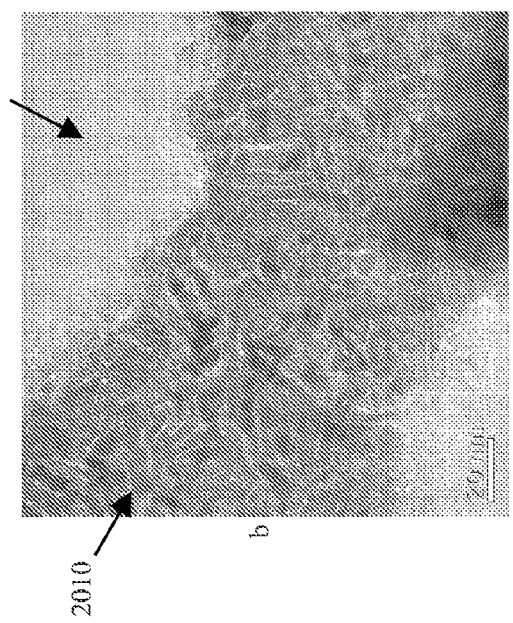
FIG 2

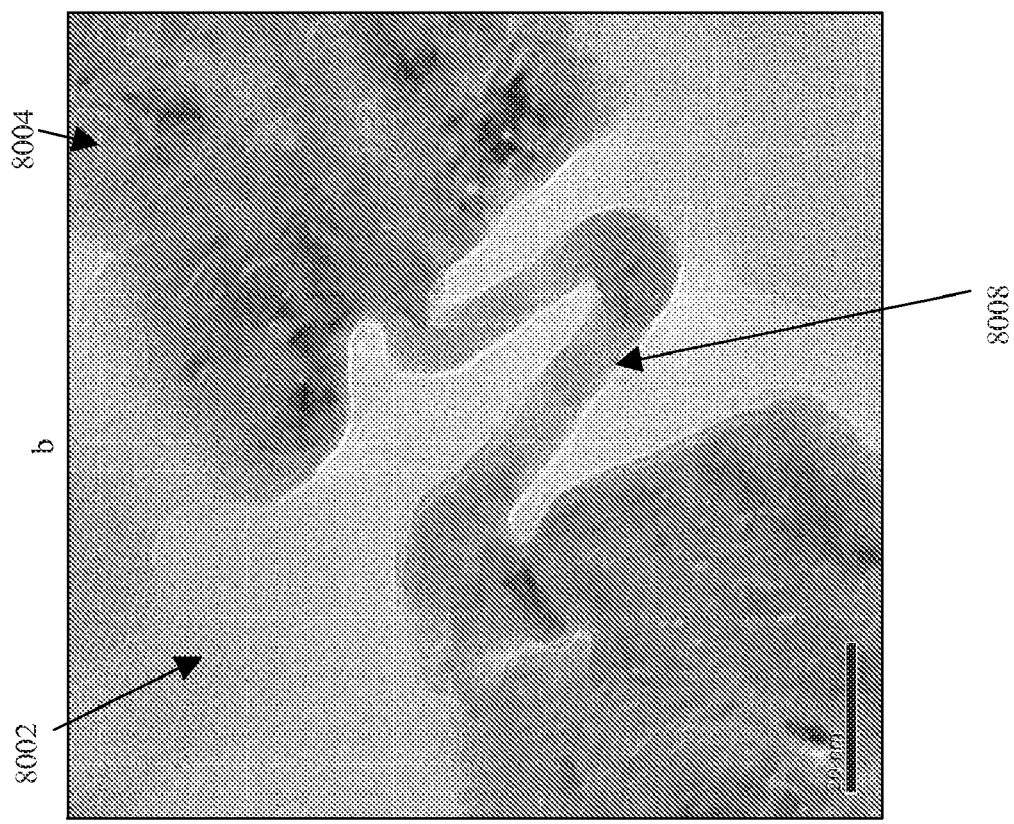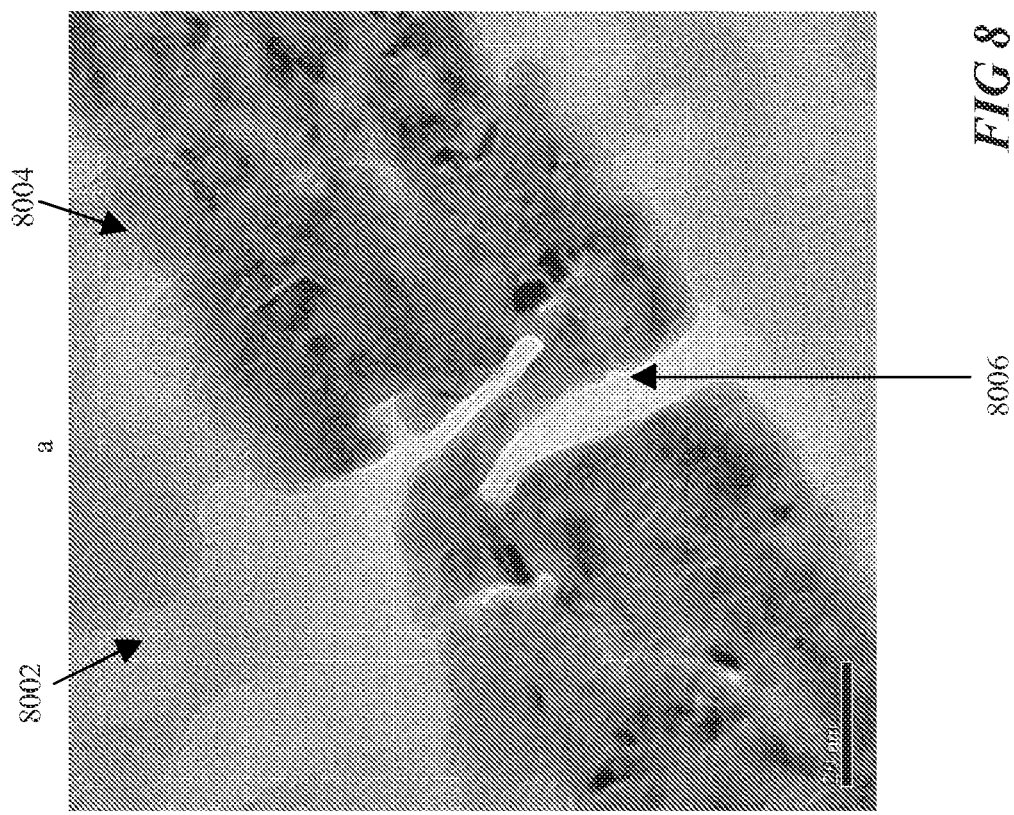
FIG 8

BEAM ABLATION LITHOGRAPHY

CROSS-REFERENCE TO RELATED APPLICATIONS

This application is the National Stage of International Application No. PCT/US2007/016006, filed Jul. 13, 2007, which application claims benefit of U.S. Provisional Application No. 60/830,904, filed Jul. 14, 2006, the entirety of each of these applications is incorporated by reference herein.

FIELD OF THE INVENTION

The present invention is generally related to the field of nanotechnology. The present invention is also related to the field of semiconductor fabrication processes, in particular the fabrication of electrodes and devices integrating nanoscale electrodes. The present invention also pertains to processes for preparing nanometer scale device features. The present invention also pertains to a variety of electronic, photonic, semiconductor and quantum effect devices.

STATEMENT OF GOVERNMENT INTERESTS

The invention was made with U.S. Government support. The Government may have certain rights in the invention under ONR Young Investigator Award No. N000140410489, American Chemical Society (ACS) PRF Award No. 41256-G10, NSF Career Award No. DMR-0449553, NSF MRSEC No. DMR00-79909 and NSF IGERT Program Grant No. DGE-0221666.

BACKGROUND OF THE INVENTION

The last few decades have witnessed myriad breakthroughs in studies on single molecules, nanometer-scale structures and quantum phenomena in general. Exciting results continue to emerge at a rapid rate and proposed applications for them are quick to follow. In order to realize these applications and pursue research at similar and even smaller scales, reliable methods are needed to electronically connect atoms, molecules, nanostructures and other components at the nanoscale. Further advancements in size reduction and geometrical control of nanostructures below about 10 nm will open unique new possibilities in the study of plasmonics, superconductivity, spintronics, and quantum electronics. Such an advancement will also open the door to a wide range of studies in nanofluidics and even has the potential to enable high speed DNA sequencing.

Transmission electron beams (TEBs) have long been used to study materials at nanometer scales and in some cases have also been shown to affect a material's structure during imaging. Although it has been know that TEBs are capable of altering nanoscale material structure, there is still an urgent need to reliably fabricate nanoscale structures with even greater accuracy and precision compared to currently existing techniques. There is also a present need for more flexible and rapid fabrication technique that can be easily inspected using TEM.

For large scale integration of many electronic components, superconducting nanowires are desirable to minimize the heat dissipation. Studies of the breakdown of superconductivity as a function of the reduced wire size is of practical importance in determining the limit to miniaturization of superconducting electronic circuits. It remains to be established whether there is a limit to how thin a superconducting wire can be before its character changes from superconducting to normal and what sets this limit. Studies of quantum suppression of superconductivity have been reported down to ~15 nm wires which were fabricated on suspended carbon nanotubes. One problem with the fabrication method using suspended carbon nanotubes is that once the superconducting nano-wire goes normal, the generated Joule heat is not efficiently removed out from the wire and the wire easily melts; consequently, it is difficult to study the normal and insulating regimes. Accordingly, there is a present need for a reliable geometrical control of local normal and superconducting regimes.

SUMMARY OF THE INVENTION

Accordingly, the present invention provides beam lithography processes, comprising: providing a supported membrane characterized as being transparent to a beam, the membrane comprising at least two surfaces; forming a surface material layer onto one of the surfaces of the membrane; orienting the surface material layer side of the support membrane facing away from a beam source; imaging the surface material layer; increasing the magnification to bring the beam to crossover at a location spatially proximate to a desired ablation location of the surface material layer; and removing surface material layer from the desired ablation location.

The present invention also provides transforming processes, comprising: providing a supported membrane characterized as being transparent to a beam, the membrane comprising at least two surfaces; forming a surface material layer onto one of the surfaces of the membrane; orienting the surface material layer side of the support membrane facing away from a beam source; imaging the surface material layer; increasing the magnification to bring the beam to crossover at a location spatially proximate to a desired location of the surface material layer; and transforming the crystal structure of the surface material layer at the desired location.

The present invention also provides a variety of devices, nanogap field effect transistors, nano-wires, nano-crystals and artificial atoms made using the disclosed methods.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 2a is a schematic illustration of a basic principle of the present invention.

FIG. 2b shows a TEM image of metal on thin film.

FIG. 2c shows a TEM image of a nano-hole.

FIG. 2d shows a TEM image of a nano-cut.

FIG. 8 shows TEM images of a variation of the application shown in FIG. 7.

DETAILED DESCRIPTION OF ILLUSTRATIVE EMBODIMENTS

Figure 1:
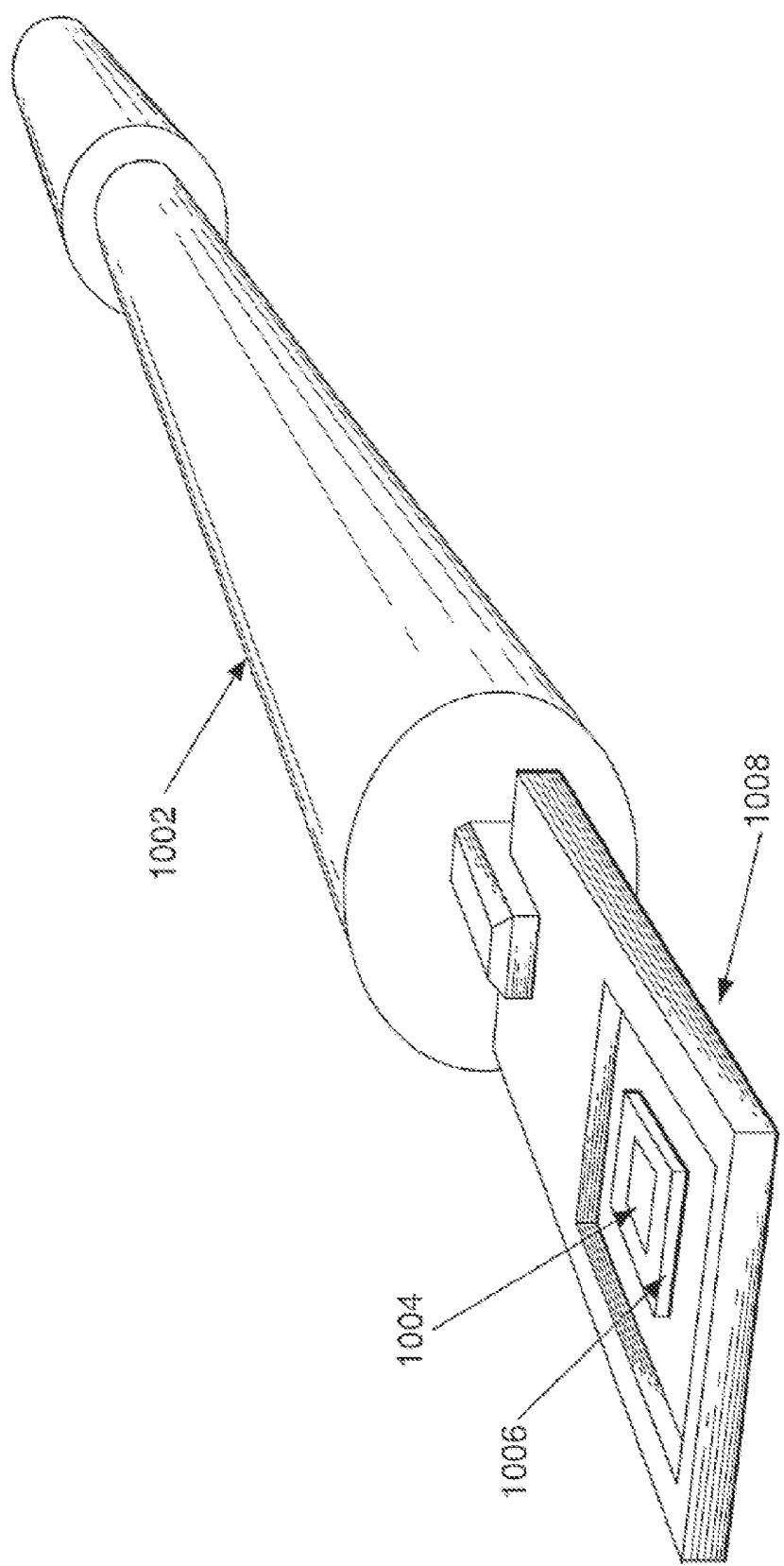
FIG. 1 is a schematic illustration of device holder used to load membrane window devices into a transmission electron microscope (TEM).

The present invention may be understood more readily by reference to the following detailed description taken in connection with the accompanying figures and examples, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

As employed above and throughout the disclosure, the following terms, unless otherwise indicated, shall be understood to have the following meanings.

"Nanoscale" refers generally to dimensions in the range of from about 0.1 nanometer ("nm") up to about 100 nm.

"Support membrane" refers generally to a thin material that is physically supported by an adjacent stronger material; "support membrane" and "thin layer support membrane" are generally synonymous as used herein.

"Surface material layer" refers generally to an initial thin surface material that is to be nano-sculpted by the ablating beam and is physically supported by a support membrane.

In the present invention, the ablating beam can be electron beams, ion beams, atom beams, neutron beams and arbitrary particle beams. In preferred embodiments, the ablating beam is transmission electron beam and the ablating beam source is provided by a transmission electron microscopy which is able to achieve about 0.1 nm resolution images. In an embodiment of present invention, the initial ablating beam can be split into multiples beams using existing methods in the art to enable parallel ablation at multiple ablation locations on the surface material layer.

The initial surface material layer is prepared to be nano-sculpted by the ablating beam. This initial surface material layer can be prepared on a thin support membrane that is by itself essentially transparent to the ablating beam. Suitable support membranes include any of a variety of thin film materials that are typically used in the field of semiconductor and photonic devices. Preferred thin film materials include silicon nitride, low-stress amorphous silicon nitride, silicon oxide, and gallium arsenide. Window grids for use in transmission electron microscopy (TEM) can be suitably used as support membranes, such as those commercially available from SPI Supplies, Inc., West Chester, Pa. (http://www.2spi.com/catalog/instruments/silicon-nitride.shtml).

Support membranes can be provided using CVD or any suitable thin film deposition processes known in the art. Accordingly, many different types of support membrane compositions and geometries are possible. For example, any of the below listed compounds and compositions, and combinations thereof, can be prepared into support membranes using methods know in the art: low stress amorphous silicon nitride, galium nitride, amorphous carbon, indium arsenide, aluminum oxide, Aeschynite (Rare Earth Yttrium Titanium Niobium Oxide Hydroxide), Anatase (Titanium Oxide), Bindheimite (Lead Antimony Oxide Hydroxide), Bixbyite (Manganese Iron Oxide), Brookite (Titanium Oxide), Chrysoberyl (Beryllium Aluminum Oxide), Columbite (Iron Manganese Niobium Tantalum Oxide), Corundum (Aluminum Oxide), Cuprite (Copper Oxide), Euxenite (Rare Earth Yttrium Niobium Tantalum Titanium Oxide), Fergusonite (Rare Earth Iron Titanium Oxide), Hausmannite (Manganese Oxide), Hematite (Iron Oxide), Ice (Hydrogen Oxide), Ilmenite (Iron Titanium Oxide), Perovskite (Calcium Titanium Oxide), Periclase (Magnesium Oxide), Polycrase (Rare Earth Yttrium Titanium Niobium Tantalum Oxide), Pseudobrookite (Iron Titanium Oxide), members of the Pyrochlore Group, such as Betafite (Rare Earths Calcium Sodium Uranium Titanium Niobium Tantalum Oxide Hydroxide), Microlite (Calcium Sodium Tantalum Oxide Hydroxide Fluoride), Pyrochlore (Sodium Calcium Niobium Oxide Hydroxide Fluoride,) Ramsdellite (Manganese Oxide), Romanechite (Hydrated Barium Manganese Oxide), members of the Rutile Group, such as Cassiterite (Tin Oxide), Plattnerite (Lead Oxide), Pyrolusite (Manganese Oxide), Rutile (Titanium Oxide), Stishovite (Silicon Oxide), Samarskite-(Y) (Rare Earth Yttrium Iron Titanium Oxide), Senarmontite (Antimony Oxide), and members of the Spinel Group, such as Chromite (Iron Chromium Oxide), Franklinite (Zinc Manganese Iron Oxide), Gahnite (Zinc Aluminum Oxide), Magnesiochromite (Magnesium Chromium Oxide), Magnetite (Iron Oxide), Spinel (Magnesium Aluminum Oxide), Taaffeite (Beryllium Magnesium Aluminum Oxide), Tantalite (Iron Manganese Tantalum Niobium Oxide), Tapiolite (Iron Manganese Tantalum Niobium Oxide), Uraninite (Uranium Oxide), Valentinite (Antimony Oxide, Zincite (Zinc Manganese Oxide), or any combination thereof. In preferred embodiments, the support membranes are suitably chosen from low-stress amorphous silicon nitride.

The thin film materials that give rise to suitable support membranes are preferably supplied as thin films on one or both sides of a silicon support wafer. Preferably the support membrane is highly polished, such that the surface roughness is less than about 10 nm per square micron. Thin film deposited silicon support wafers are subsequently processed to remove portions of the silicon support to yield silicon-supported thin films. Thin film etching can also be carried out to control the thickness of the resulting thin film support membrane.

Suitable support membranes typically have a thickness in the range of from about 0.1 nm to about 1000 nm and can be unsupported, but are preferably supported on a substrate such as silicon. Suitable support membranes supported on a substrate form a free-standing support membrane window. Free-standing support membrane windows that can be suitably used in various embodiments of the present invention typically have an area in the range of from about $10^{-1}$ square microns to about $10^5$ square microns. There is nothing in principle that prevents the window from being arbitrarily small or large, so any size is possible, from about 100 square nanometers up to about 1 square millimeter. The free-standing support membrane window can have almost any, shape, such as a circle, square, rectangle, triangle, or other polygon having 4 or more sides. In preferred embodiments, the support membranes have a thickness of from about 20 to 60 nm. Further information about preparing support membranes can be found in Grant, A. W., et al., *Nanotechnol.* 2004, 15, 1175; Morkved, T. L., et al., *Polymer* Vol. 39 No. 16 pp. 3871-3875, 1998; and Pandey, R. K., et al., *J. Opt. Mat.* 2004, 27, 139. A plurality of support membranes can also be provided on wafers.

The initial surface material layer that will be nano-sculpted by the ablating beam can be any solid. Preferred surface materials include: aluminum, chromium, nickel and silver. Any of the below listed can be prepared as surface material layer: aluminum, chromium, nickel, silver, iron, manganese, cobalt, titanium, copper, gold, silicon, carbon, carbon nanotubes, graphene, silicon nitride, low stress amorphous silicon nitride, gallium nitride, amorphous carbon, indium arsenide, aluminum oxide, Rare Earth Yttrium Titanium Niobium Oxide Hydroxide, Titanium Oxide, Lead Antimony Oxide Hydroxide, Manganese Iron Oxide, Titanium Oxide, Beryllium Aluminum Oxide, Iron Manganese Niobium Tantalum Oxide, Aluminum Oxide, Copper Oxide, Rare Earth Yttrium Niobium Tantalum Titanium Oxide, Rare Earth Iron Titanium Oxide, Manganese Oxide, Iron Oxide, Hydrogen Oxide, Iron Titanium Oxide, Calcium Titanium Oxide, Magnesium Oxide, Rare Earth Yttrium Titanium Niobium Tantalum Oxide, Iron Titanium Oxide, a member of the Pyrochlore Group, a member of the Rutile Group: Cassiterite Tin Oxide, Plattnerite Lead Oxide, Pyrolusite Manganese Oxide, Rutile Titanium Oxide, Stishovite Silicon Oxide, Samarskite-Y Rare Earth Yttrium Iron Titanium Oxide, Senarmontite Antimony Oxide, a member of the Spinel Group, or any combination thereof.

The initial surface material layer that will be nano-sculpted by the ablating beam can be formed onto one side of the support membrane surface by using existing methods such as electron beam and photo lithography. A suitable surface material layer has a thickness in the range of from about 10 nm to about 50 nm. In preferred embodiments, surface material layers have a thickness in the range of from about 10 nm to about 50 nm and have a form in the shape of thin strips.

The surface material layer side of the support membrane faces away from and perpendicular to the source of the beam. As far as imaging, the membrane can be either face up or down. The image collection system typically does not distinguish between the two orientations. It is sometimes beneficial to orient the surface material layer side of the support membrane face-down so that, upon being exposed to the intense ablating beam, removed portion of the surface material layer is "pushed off" of the surface instead of being "mashed into" the surface, as could be the case if the support membrane were face-up.

The present invention can further comprise a step of identifying a desired location on the surface material layer to be ablated. The identifying step can be conducted using the standard imaging modes of the microscope with magnifications typically below 100,000×, or below 80,000×, or below 60,000×, or even below about 40,000×, and with reduced beam intensity, that is not sufficient to result in any ablation.

After identifying a desired location on the surface material layer, the magnification is increased, for example as high as 200,000×, or even 300,000×, or even 400,000×, or even 500,000×, or even 600,000×, or even 700,000×, or even as high as 800,000×. The ablating beam can be brought to crossover several nanometers away from the metal for last minute sharpening of the caustic spot. Depending on the sensitivity of the surface material to the ablating beam, the distance between the beam and the surface material layer can be in a range of from about 1 nm to about 5000 nm, or between 2 and 2500 nm, or between 4 and 1000 nm, or even between 8 and 500 nm. Once the caustic spot is made as small as possible, the beam can be aimed at the desired location on the surface material layer to be ablated to perform the actual ablation. If at any time it is desirable to end the ablation, the beam need only be broadened away from crossover and the ablation will stop almost immediately.

The present invention can be conducted using computerized control which would allow for greater precision and more rapid fabrication. The computerized control can be facilitated by using the current density that passes through surface material layer and support membrane as a feedback control. The current density will be lower if the ablating beam is over an area of surface material layer plus support membrane than it is over support membrane only. When the ablating beam is over an area of surface material layer plus the support membrane, the current density will increase as ablation proceeds and therefore the computer, which is able to read the current density and also control the spot that the ablating beam is over, is then able to know where the ablating beam is with respect to the edges of the surface material layer and can sense the ablation action in real time.

In an embodiment of a device fabricated with the present invention, a robust geometrical control can be achieved to vary dimensions of a nano-wire. A nano-wire with modulated diameter along its length would have modulated local regions of normal and superconducting behavior; for a nano-wire with modulated regions larger than some critical size, the modulated width will result in periodically modulated critical temperature along the wire length. Different materials can be made as electrodes to create S-N and S-I modulated wires, and use normal and/or superconducting electrodes. Modulation of electrodes (whether one or both are normal or superconducting) will put these devices in different universality classes and would allow the study of quantum phase transitions.

Sometimes if the intensity of the ablating beam is not strong enough to result in actual ablation, a portion of the surface material layer that is exposed to the narrowly focused ablating beam can be moved by the beam on the support membrane. In an embodiment of a device fabricated with the present invention, a nano-island of a surface material can be moved by a narrowly focused electron beam between two electrodes on a support membrane. The nano-island of surface material can also be welded to one of the two electrodes by the narrowly focused electron beam.

The present invention can be used to change the crystal structure of the surface material. In one embodiment of present invention, a submonolayer of amorphous metallic islands supported on a thin support membrane can be transformed into partially crystalline and ultimately single crystalline by a narrowly focused electron beam.

FIG. 1 is a schematic illustration of device holder used to load membrane window devices into a transmission electron microscope (TEM). A device (1006) comprising a membrane window (1004) can be placed face down on a "blade" (1008) that can be itself held by a holder arm (1002). The blade (1008) has a hole in it (not shown) that can be aligned to the location of the membrane window (1004) to allow the electron beam to pass completely through.

FIG. 2a is a schematic illustration of a basic principle of the invention. Metal (2002) sits on a thin film (2008) and can be exposed to an electron beam (2006) which removes metal from the exposed region. A possible structure (2004) is shown being formed by the electron beam (2006). FIG. 2b shows an actual TEM image of metal (2010) on thin film (2014). FIG. 2c and 2d shows actual TEM images of a nano-hole (2012) and a nano-cut (2014) on the metal (2010) created by the present invention.

Figure 3:
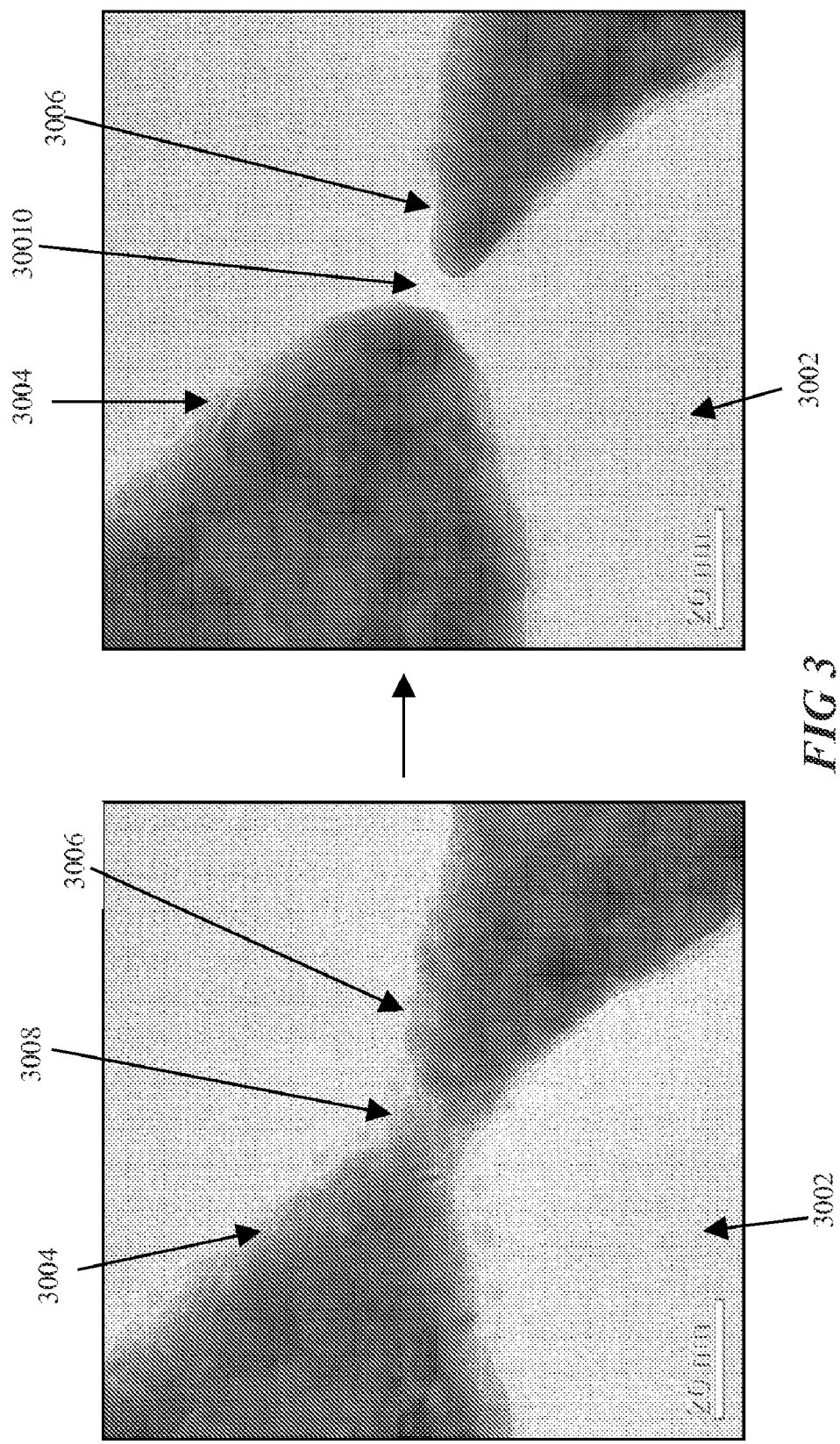
FIG. 3 shows TEM images of an application of the present invention to remove a narrow segment of metal.

FIG. 3 shows TEM images of an application of the present invention to remove a narrow segment of metal connecting two large segments of metal. On a thin film (3002) two large segments of metal (3004 and 3006) are connected by a narrow segment of metal (3008). By using the present invention, the narrow segment (3008) can be removed, leaving a gap (3010).

Figure 4:
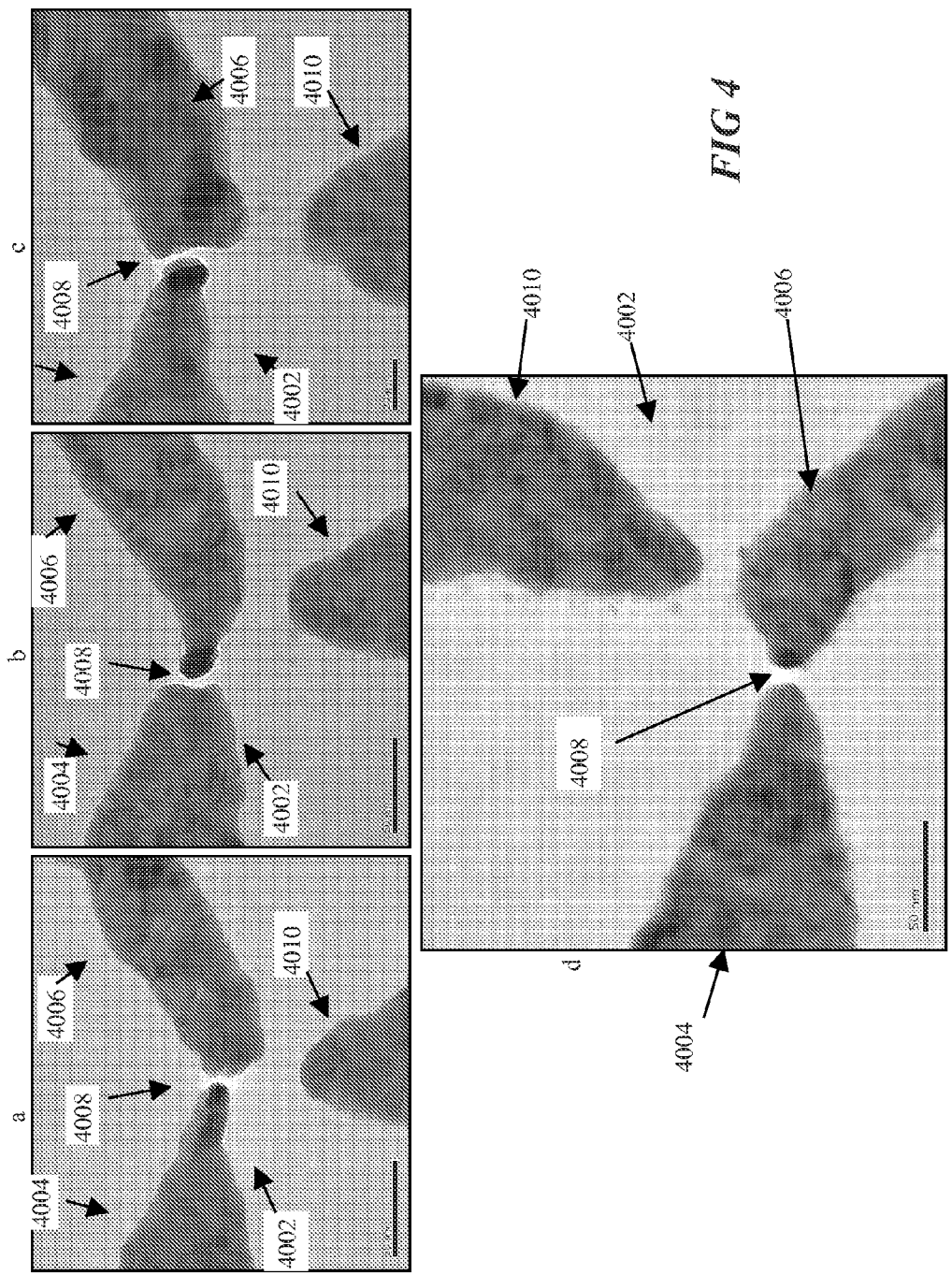
FIG. 4 shows TEM images of an embodiment of a device fabricated with the present invention in which a nano-hole is created in a nano-gap region.

FIG. 4 shows TEM images of an embodiment of a device fabricated with the present invention in which a hole is created in a nano-gap region. The figure shows four examples of the same device design. On a thin film (4002) three metallic segments are arranged to achieve a nanogap field effect transistor (NGFET). The NGFETs consist of a source electrode (4004), a drain electrode (4006) and a gate electrode (4010). By using the present invention a hole (4008) can be created directly in the nanogap region. An application of this device is detailed electronic characterization of molecules. It is envisioned that by allowing a molecule to pass through the hole, the source (4004) and drain (4006) electrodes can, at any moment during the molecule's translocation, measure the conductivity of the segment of the molecule that is in the nano-gap at that moment. In particular, high-speed DNA sequencing is enabled with this embodiment. The conductivity of the bases of DNA (C, G, T, A) are predicted to be different enough that direct electrical measurements can resolve the base sequence of DNA as it is translocated through the gap.

Figure 5:
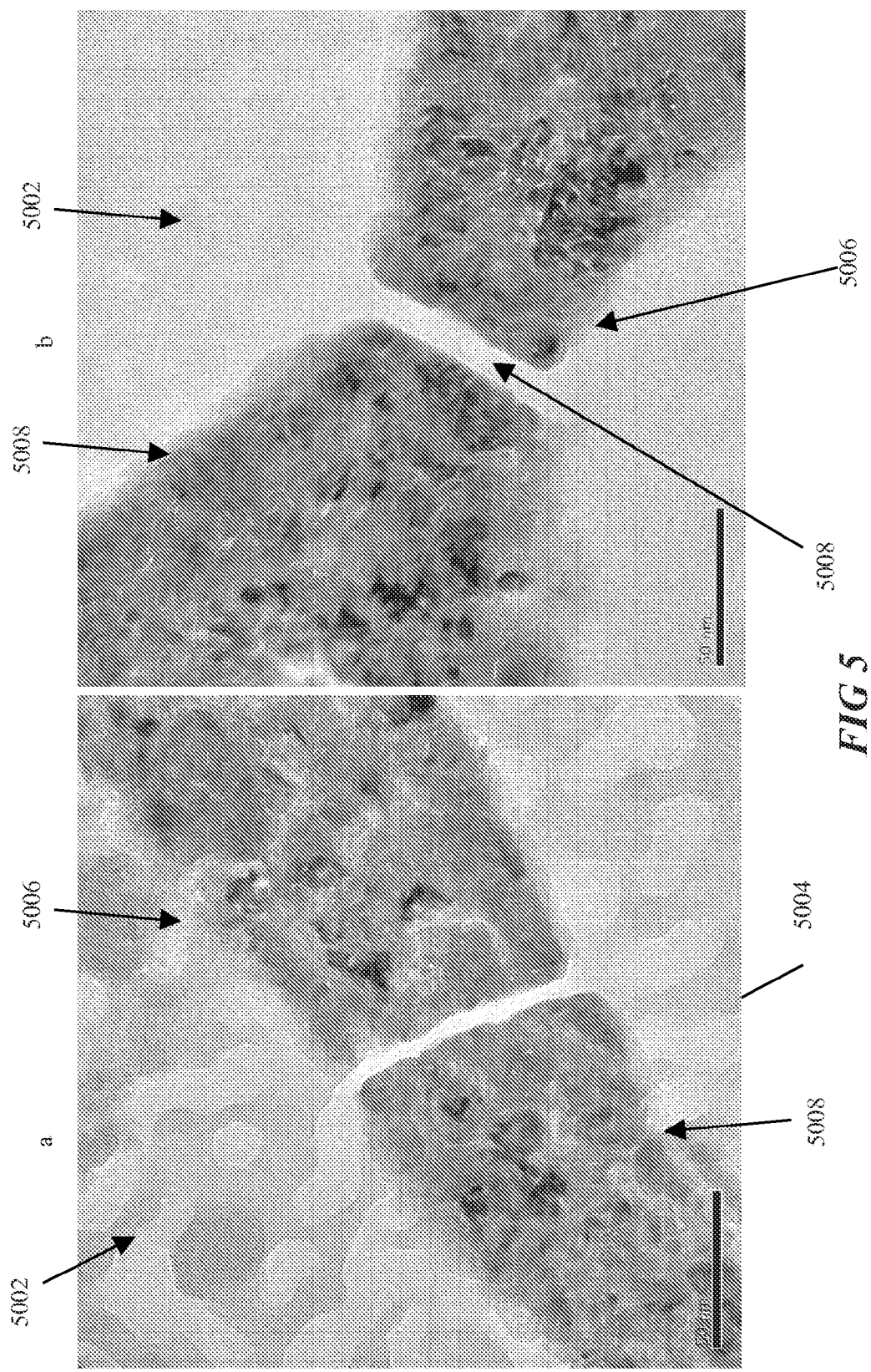
FIG. 5 shows TEM images of an application of the present invention to create narrow channels through metal.

FIG. 5 shows TEM images of an application of the present invention to create narrow channels through metal. On a thin film (5002) a narrow channel (5008) is created through a large segment of metal, thereby dividing the large metal segment into two smaller segments (5008 and 5006).

Figure 6:
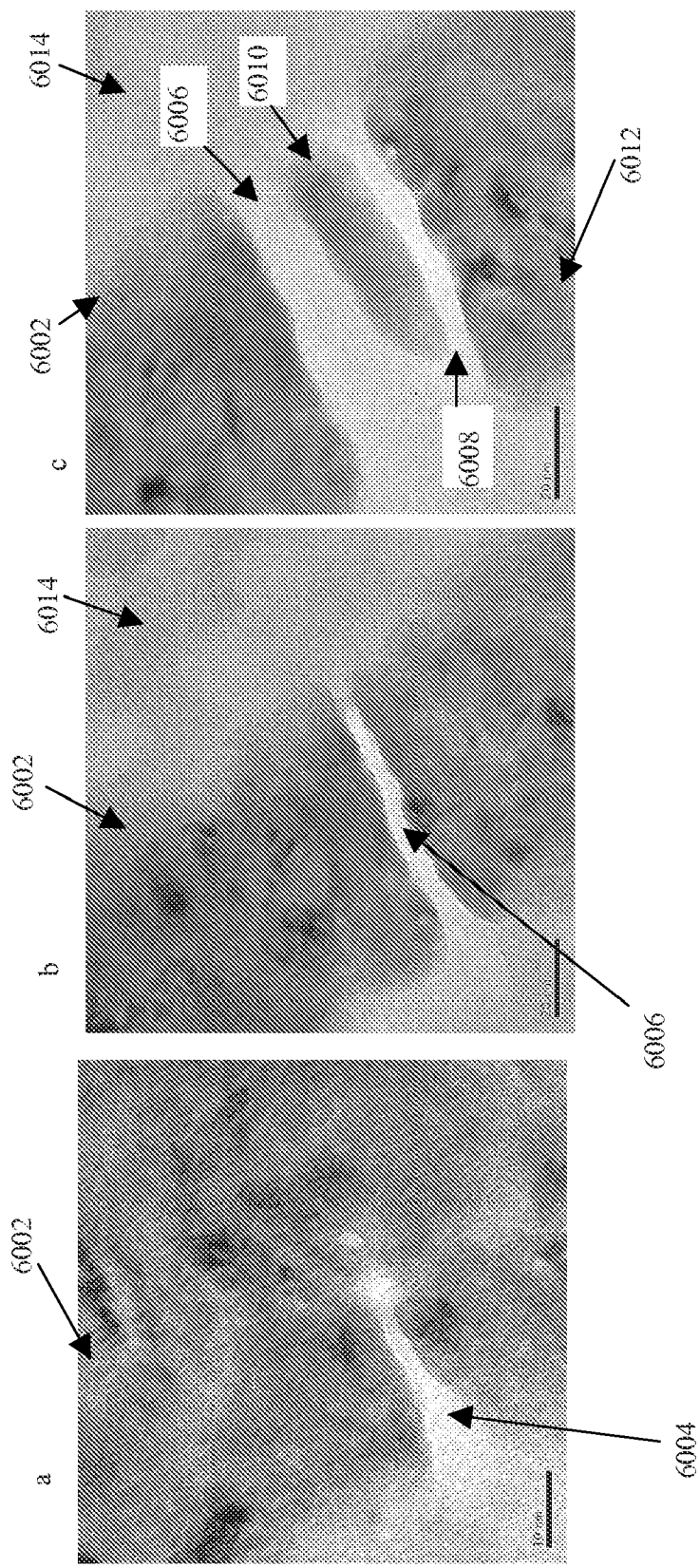
FIG. 6 shows TEM images of an application of the present invention to create particles by cutting out regions from a larger segment of material.

FIG. 6 shows TEM images of an application of the present invention to create particles by cutting out regions from a larger segment of material. Metal (6002) is changed by using the present invention to initially cut partially (6004) and then completely (6006) through. Another complete cut through is made nearby (6008) thereby creating a nano-particle (6010) in between the two remaining segments of the initial material (6002 and 6012). All material is shown on a thin film (6014).

Figure 7:
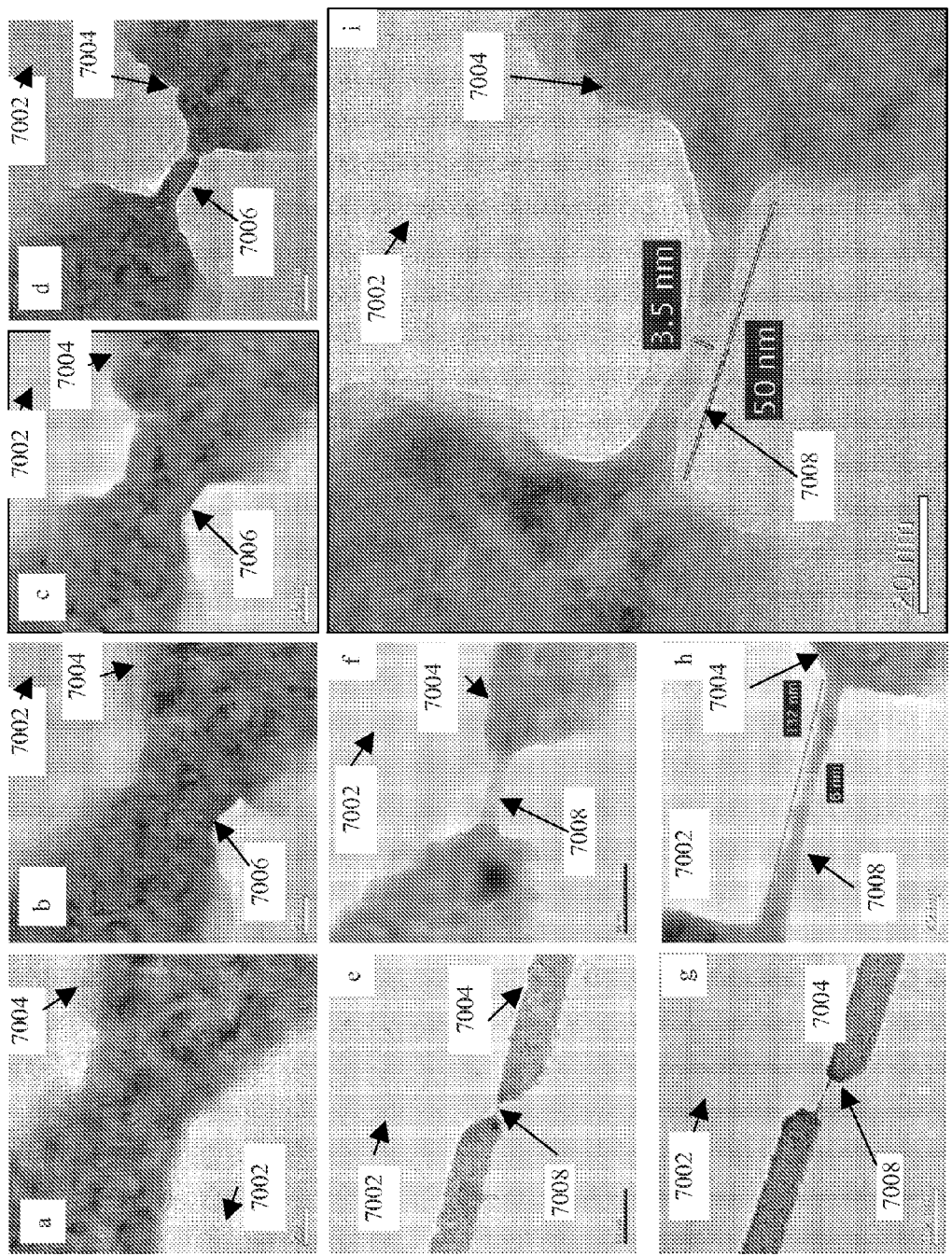
FIG. 7 shows TEM images of an application of the present invention to create nano-wires.

FIG. 7 shows TEM images of an application of the present invention to create nano-wires. On a thin film (7002), regions are removed from a large segment of material (7004). Various stages of removing these regions to yield a nano-wire are shown (7006). Examples of completed nanowires are shown (7008). In these examples the nanowires are connected smoothly to large segments (7004) which can be used as source and drain electrodes to perform measurements or manipulate the state of the nano-wire electronically. This application can be used to generate local electric and magnetic fields which may be used to manipulate the position or physical state of a targeted object or collection of objects.

FIG. 8 shows TEM images of a non-straight geometry nano-wire, a variation of the application shown in FIG. 7. From the large segment of material (8004) the serpentine wire (8008) is shown in the process of being created (8006). The background is a thin film (8002). This device can be used to generate local electric and magnetic fields which may be used to manipulate the position or physical state of a targeted object or collection of objects.

Figure 9:
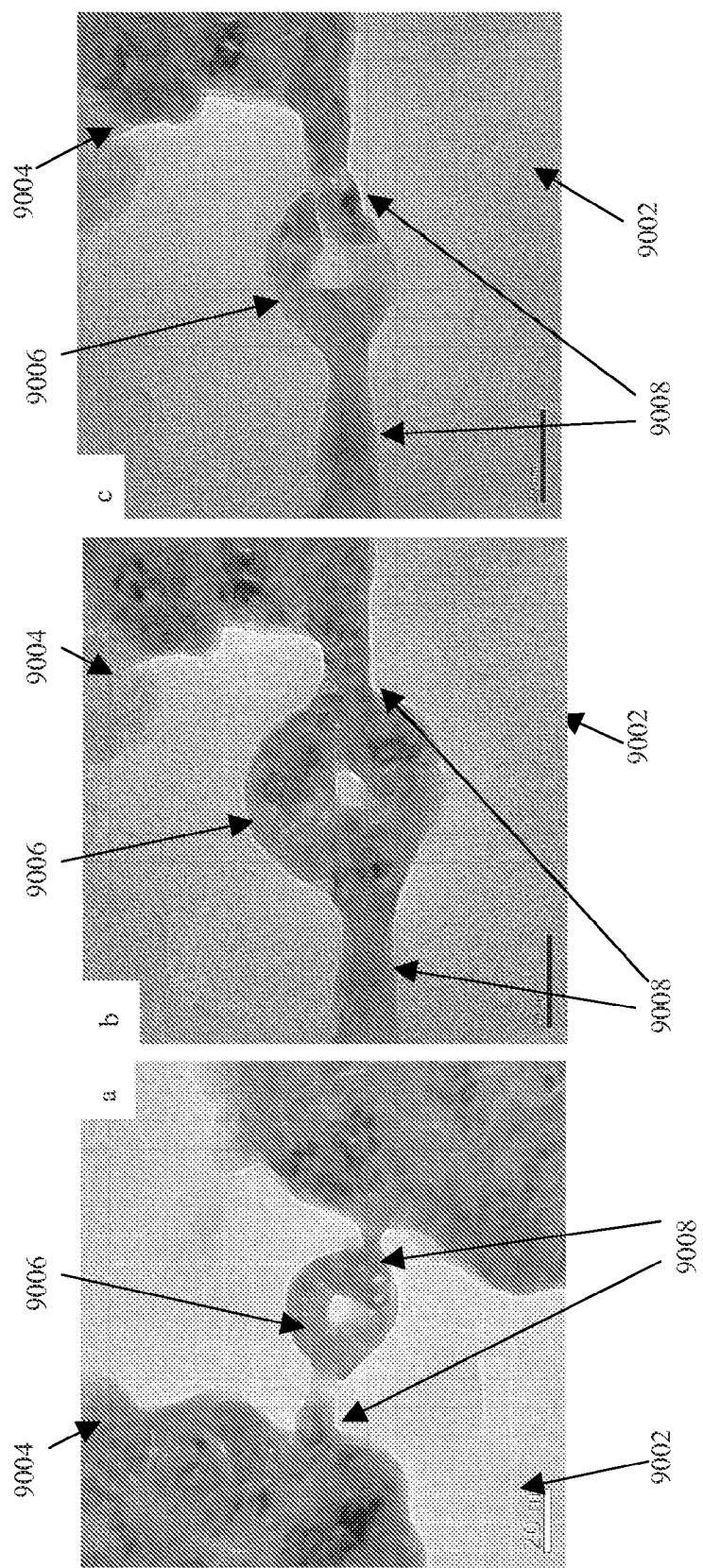
FIG. 9 shows TEM images of an embodiment of a device fabricated with the present invention in which a nanometer-scale ring is created.

FIG. 9 shows TEM images of an embodiment of a device fabricated with the present invention in which a nanometer-scale ring is created. From a large segment of material (9004), the present invention was used to remove material until the ring (9006) is formed. In these examples, the ring is connected to the initial material (9004) by nanowires (9008). This device can be used to generate local electric and magnetic fields which may be used to manipulate the position or physical state of a targeted object or collection of objects. For example, a nano-ring of the type shown in 9000 may be used to trap atoms and cool them. The ring sits on a thin film (9002) and it is possible to remove this thin film by chemical or mechanical treatments to yield a free standing ring held by nanowires (9008) connected to the initial metal (9004).

Figure 10:
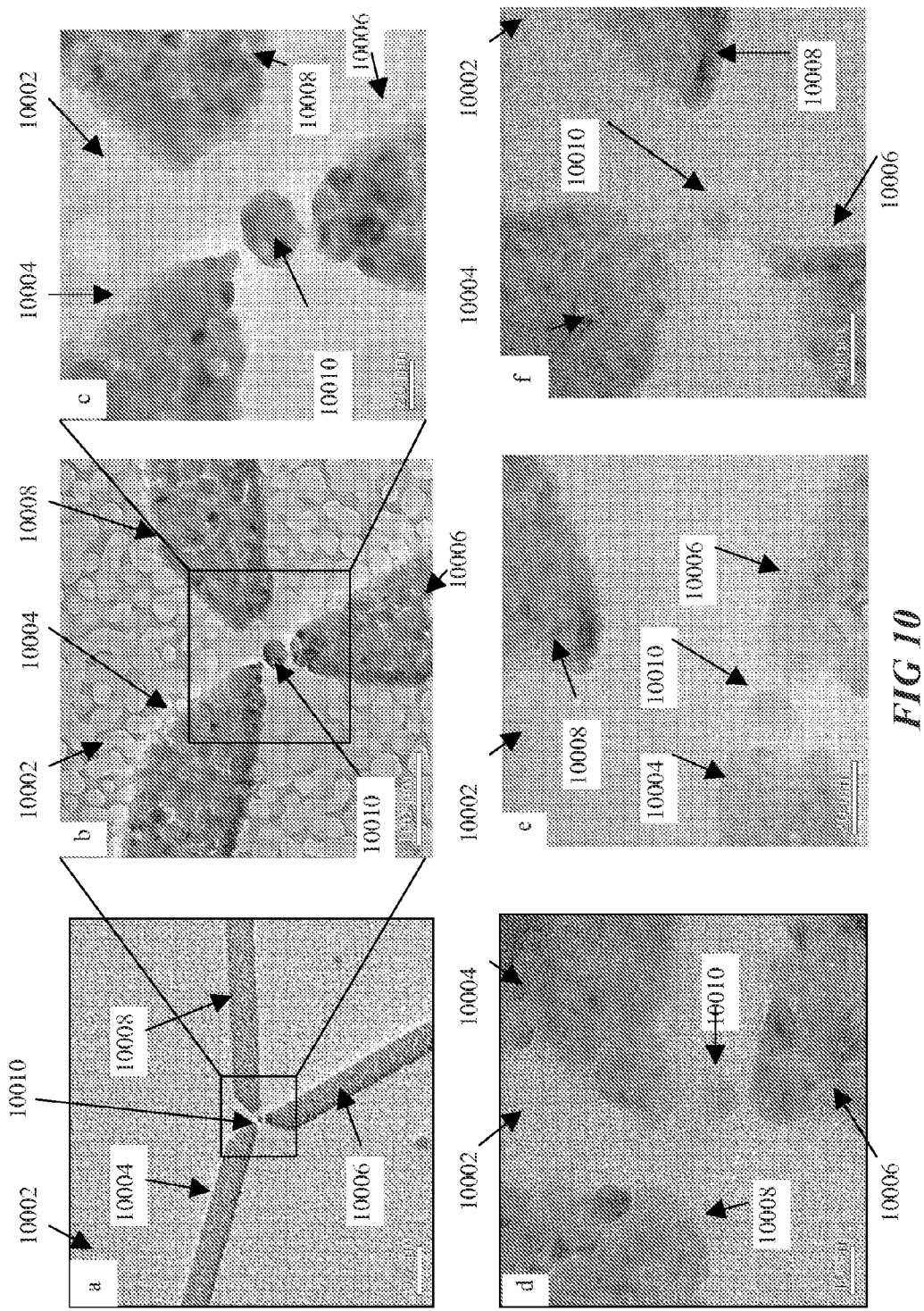
FIG. 10 shows TEM images of an embodiment of a device fabricated with the present invention in which three terminal devices based on "artificial atoms" are created.

FIG. 10 shows TEM images of an embodiment of a device fabricated with the present invention in which three terminal devices based on "artificial atoms" are created. On a thin film (10002) source (10004), drain (10006) and gate (10008) electrodes are made with the present invention in close proximity to an "island" (10010) that is also made with the present invention, but could have been prepared otherwise. Small islands made of metal and/or semiconducting material behave as "artificial atoms" and the presence of the three electrodes allows for the detection of the physical state of the island as well as the controlled manipulation of its physical state. This device may be used as a sensor if the island is designed to be (or discovered to be) sensitive to some agent material. Quantum information processing may be achieved with this type of device. Furthermore, it is possible to create more complicated structures consisting of many islands, source, drain and gate electrodes. Such devices may behave as controllable "artificial molecules." These devices may also be used for information processing.

Figure 11:
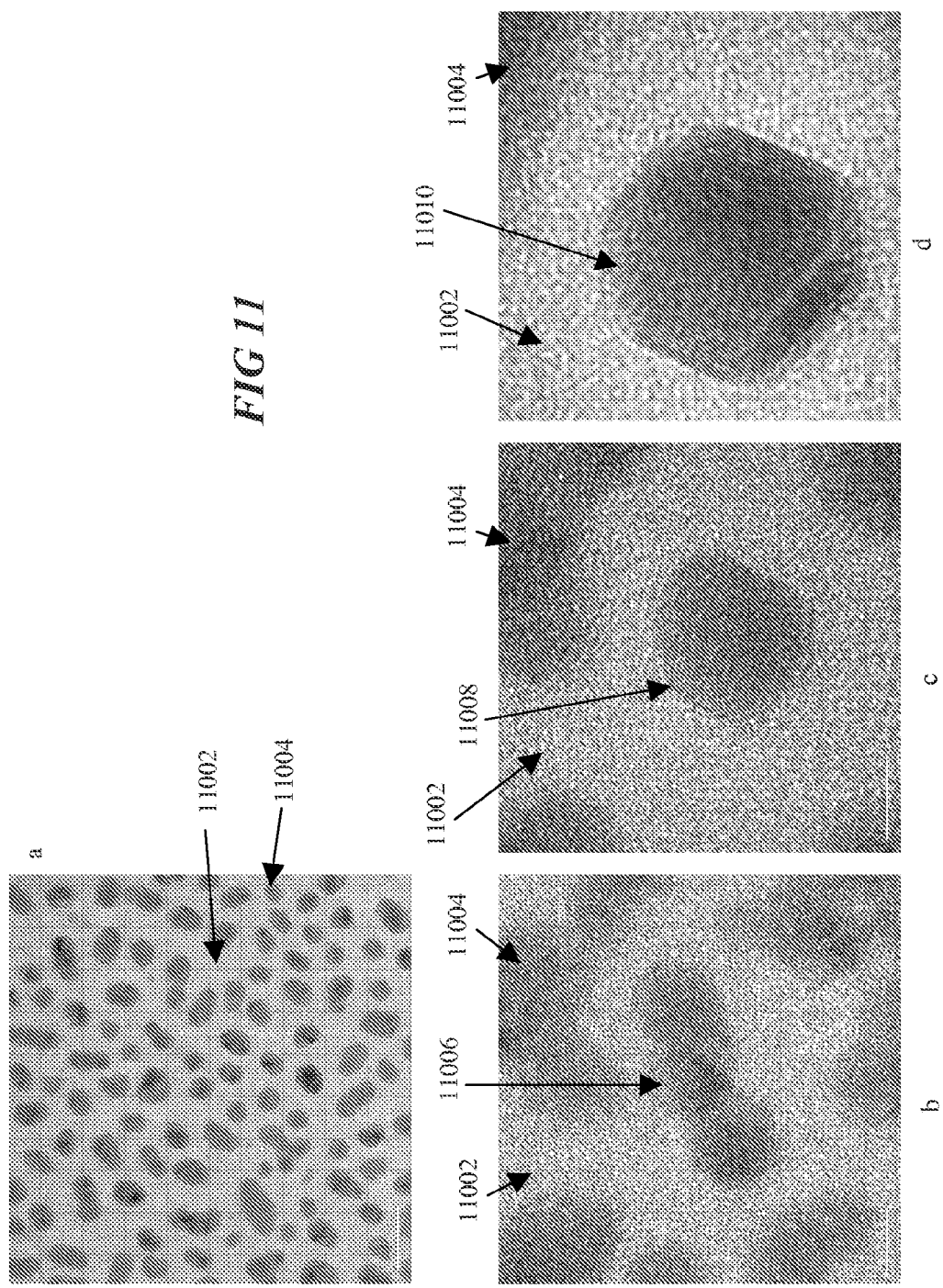
FIG. 11 shows TEM images of an application of the present invention to create nano-crystals.

FIG. 11 shows TEM images of an application of the present invention to create nano-crystals. A sub-monolayer of amorphous metallic islands was prepared by evaporation of a thin film of gold onto a thin film (11002). Slowly (<0.5 nm/sec) evaporating a thin film (<10 nm) of metal yields a sub-monolayer of amorphous islands (11004). Exposing an initially amorphous island (11006) to the electron beam (not shown) transforms the island into partially crystalline (11008) and ultimately single crystalline (11010).

Figure 12:
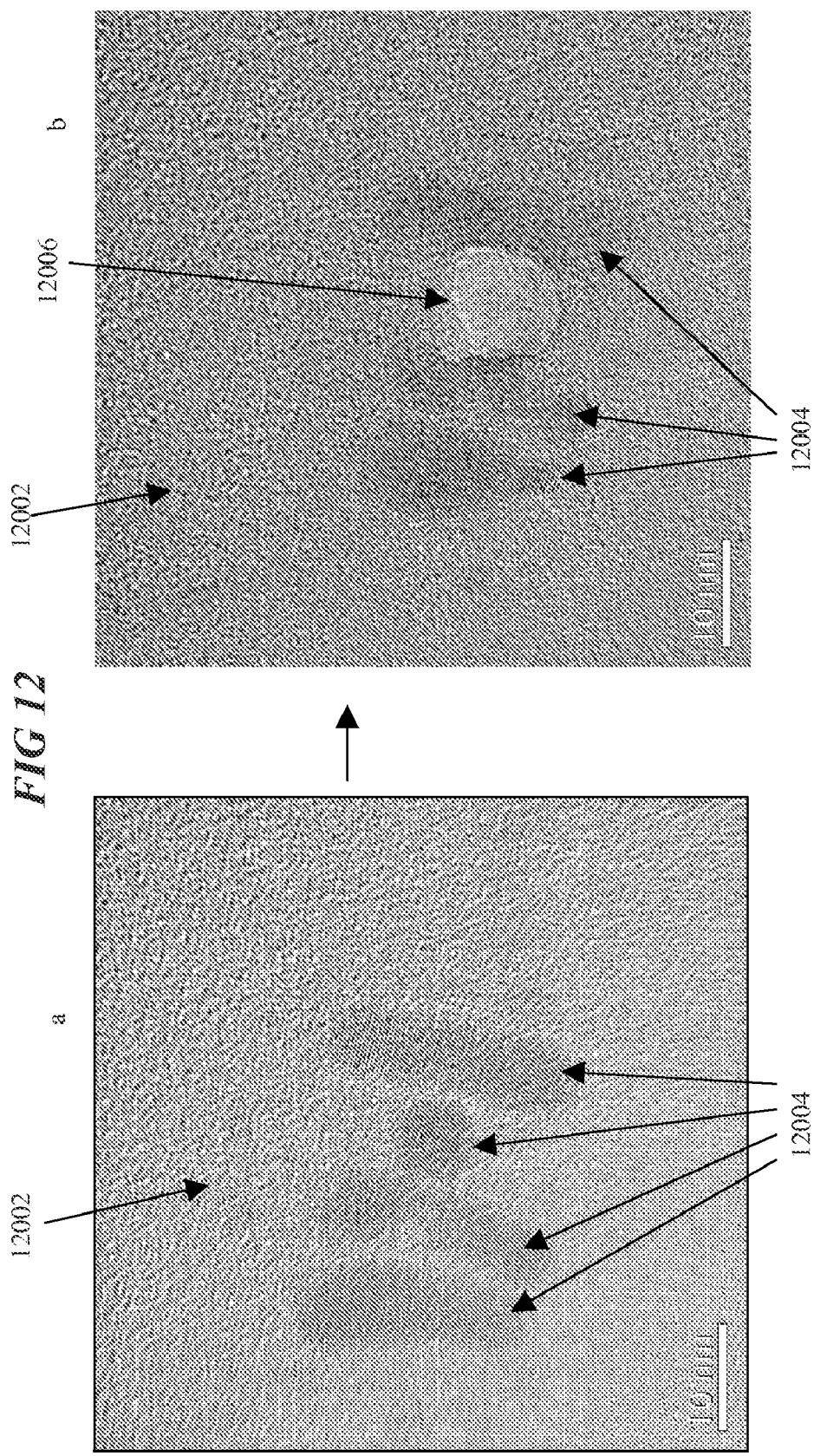
FIG. 12 shows TEM images of an application of the present invention to remove nano-particles from a surface.

FIG. 12 shows TEM images of an application of the present invention to remove nano-particles from a surface. Nano-crystals (12004) are shown on a thin film (12002). Exposure of one nano-crystal to the narrowly focused electron beam served to remove it from the surface (12006).

Figure 13:
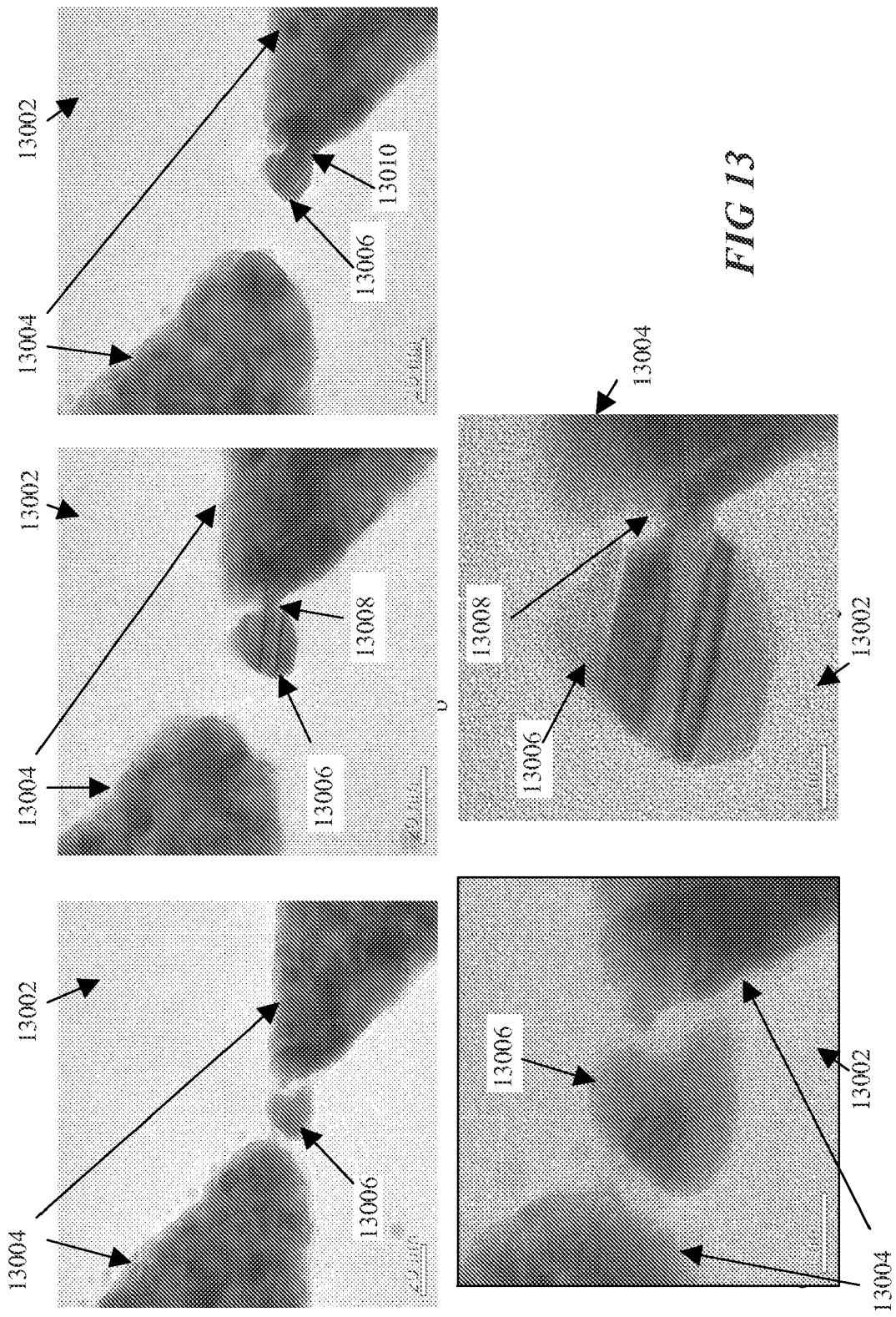
FIG. 13 shows TEM images of an application of the present invention to move and weld materials.

FIG. 13 shows TEM images of an application of the present invention to move and weld materials. An island of material (13006) is on a thin film (13002) situated between two electrodes (13004). The island is moved by the narrowly focused electron beam and welded to one of the electrodes (13008).

Additional exposure of the region marked as 13008 leads to enhanced fusion of the island to the electrode (13010).

Examples and Other Illustrative Embodiments

In these examples, ablating lithography was performed on thin low-stress amorphous silicon nitride support membrane. The thickness of thin support membrane was about 40 nm. The ablating beam was provided by a JEOL 2010F Transmission Electron Microscopy (TEM). The smallest attainable beam diameter on this instrument was about 0.5 mm. Production of wafers with well defined square regions of free-standing insulator-only material is straightforward to achieve and easy to make in large numbers. They are also available commercially from Structure Probe, Inc. (SPI), West Chester, Pa., http://www.2spi.com/.

An initial metal that was to be nano-sculpted was patterned onto the support membrane in the form of thin strips using existing methods such as electron beam and photo lithography. The thickness of the metal thin strips are in the range of from about 10 nm to 50 nm. The membrane was then loaded into the TEM chamber with the metallized side facing away from and perpendicular to the source of the electron beam (i.e. face-down). Using the standard imaging modes of the TEM, a desired location on the metal was identified while imaging at magnifications below 100,000× and with reduced beam intensity, where no ablation was observed. After the ablation location was identified, the magnification was then increased to about 800,000× and the electron beam was brought to crossover (i.e. the minimum beam diameter) several nanometers away from the metal for last minute sharpening of the caustic spot. Without computerized assistance, it took less than 10 seconds to achieve the smallest caustic spot. Then the electron beam was aimed at the caustic spot and the actual ablation occurred. During the actual ablation, the diameter of the beam was about 0.5 nm and the intensity of the beam was about $50\times10^{-12}$ A/cm$^2\cdot$s. When the electron beam was broadened away from crossover, the ablation stopped almost immediately.

What is claimed is:

1. A beam lithography process, comprising:
   providing a supported membrane characterized as being transparent to a beam, the membrane comprising at least two surfaces;
   forming a surface material layer onto one of the surfaces of the membrane;
   orienting the surface material layer side of the support membrane facing away from a beam source;
   imaging the surface material layer;
   increasing the magnification to bring the beam to crossover at a location spatially proximate to a desired ablation location of the surface material layer; and
   removing surface material layer from the desired ablation location.

2. The process of claim 1, wherein the support membrane has a thickness in the range of from about 0.1 nm to about 1000 nm.

3. The process of claim 2, wherein the support membrane has a thickness in the range of from about 0.1 nm to about 1 nm.

4. The process of claim 2, wherein the support membrane has a thickness in the range of from about 1 nm to about 10 nm.

5. The process of claim 2, wherein the support membrane has a thickness in the range of from about 10 nm to about 50 nm.

6. The process of claim 2, wherein the support membrane has a thickness in the range of from about 20 nm to about 40 nm.

7. The process of claim 2, wherein the support membrane has a thickness in the range of from about 25 nm to about 35 nm.

8. The process of claim 1, wherein the support membrane is supported on a substrate.

9. The method of claim 8, wherein the support membrane supported on the substrate forms a free-standing support membrane window.

10. The method of claim 9, wherein the free-standing support membrane window has an area in the range of from about $10^{-1}$ square microns to about $10^5$ square microns.

11. The method of claim 9, wherein the free-standing support membrane window is in the shape of a circle, square, rectangle, triangle, or other polygon having 4 or more sides.

12. The process of claim 8, wherein the support membrane comprises silicon nitride, low stress amorphous silicon nitride, gallium nitride, amorphous carbon, indium arsenide, aluminum oxide, Rare Earth Yttrium Titanium Niobium Oxide Hydroxide, Titanium Oxide, Lead Antimony Oxide Hydroxide, Manganese Iron Oxide, Titanium Oxide, Beryllium Aluminum Oxide, Iron Manganese Niobium Tantalum Oxide, Aluminum Oxide, Copper Oxide, Rare Earth Yttrium Niobium Tantalum Titanium Oxide, Rare Earth Iron Titanium Oxide, Manganese Oxide, Iron Oxide, Hydrogen Oxide, Iron Titanium Oxide, Calcium Titanium Oxide, Magnesium Oxide, Rare Earth Yttrium Titanium Niobium Tantalum Oxide, Iron Titanium Oxide, a member of the Pyrochlore Group, a member of the Rutile Group Cassiterite Tin Oxide, Plattnerite Lead Oxide, Pyrolusite Manganese Oxide, Rutile Titanium Oxide, Stishovite Silicon Oxide, Samarskite-Y Rare Earth Yttrium Iron Titanium Oxide, Senarmontite Antimony Oxide, a member of the Spinel Group, or any combination thereof.

13. The method of claim 12, wherein the support membrane comprises silicon nitride, low stress amorphous silicon nitride, gallium nitride, amorphous carbon, indium arsenide, aluminum oxide, or any combination thereof.

14. The method of claim 12, wherein the support membrane is characterized as having a surface roughness of less than about 10 nm height variation per square micron.

15. The process of claim 1, wherein the surface material layer comprises aluminum, chromium, nickel, silver, iron, manganese, cobalt, titanium, copper, gold, silicon, carbon, carbon nanotubes, graphene, silicon nitride, low stress amorphous silicon nitride, gallium nitride, amorphous carbon, indium arsenide, aluminum oxide, Rare Earth Yttrium Titanium Niobium Oxide Hydroxide, Titanium Oxide, Lead Antimony Oxide Hydroxide, Manganese Iron Oxide, Titanium Oxide, Beryllium Aluminum Oxide, Iron Manganese Niobium Tantalum Oxide, Aluminum Oxide, Copper Oxide, Rare Earth Yttrium Niobium Tantalum Titanium Oxide, Rare Earth Iron Titanium Oxide, Manganese Oxide, Iron Oxide, Hydrogen Oxide, Iron Titanium Oxide, Calcium Titanium Oxide, Magnesium Oxide, Rare Earth Yttrium Titanium Niobium Tantalum Oxide, Iron Titanium Oxide, a member of the Pyrochlore Group, a member of the Rutile Group: Cassiterite Tin Oxide, Plattnerite Lead Oxide, Pyrolusite Manganese Oxide, Rutile Titanium Oxide, Stishovite Silicon Oxide, Samarskite-Y Rare Earth Yttrium Iron Titanium Oxide, Senarmontite Antimony Oxide, a member of the Spinel Group, or any combination thereof.

16. The process of claim 1, wherein the surface material layer is in the form of thin strips.

17. The process of claim 16, wherein the thin strip has a thickness in the range of from about 10 nm to about 50 nm.

18. The process of claim 17, wherein the thin strip has a thickness in the range of from about 20 nm to about 40 nm.

19. The process of claim 17, wherein the thin strip has a thickness in the range of from about 25 nm to about 35 nm.

20. The process of claim 1, wherein the beam comprises electron beam, ion beam, atom beam, neutron beam and arbitrary particle beam.

21. The process of claim 20, wherein the electron beam comprises transmission electron beam and scanning electron beam.

22. The process of claim 1, wherein said imaging step is conducted at a magnification below 100,000×.

23. The process of claim 1, wherein the surface material layer side of the membrane is oriented perpendicular to the beam source.

24. The process of claim 1, further comprising a step of identifying the desirable ablation location on the surface material layer at least prior to said step of increasing the magnification.

25. The process of claim 1, wherein the magnification is increased to about 800,000× after the surface material layer is imaged.

26. The process of claim 1, wherein the beam is brought to crossover to optimize the focus of the beam at a location about 1 nm to about 5000 nm away from the desired ablation location of the surface material layer.

27. The process of claim 1, further comprising a step of moving the beam away from crossover to stop said step of removing surface material layer from the desired ablation location.

28. The process of claim 1, wherein the step of removing the surface material layer from the desired ablation location is conducted automatically using computerized control.

29. The process of claim 28, wherein the computerized control is conducted by using the current density that passes through the surface material layer and support membrane as a feedback to a controlling computer.

30. The process of claim 1, wherein the beam is split into multiple beams.

31. A transforming process, comprising:
    providing a supported membrane characterized as being transparent to a beam, the membrane comprising at least two surfaces;
    forming a surface material layer onto one of the surfaces of the membrane;
    orienting the surface material layer side of the support membrane facing away from a beam source;
    imaging the surface material layer;
    increasing the magnification to bring the beam to crossover at a location spatially proximate to a desired location of the surface material layer; and
    transforming the crystal structure of the surface material layer at the desired location.

32. A device made according to the process of claim 1.

33. A device made according to the process of claim 31.

34. A nanogap field effect transistor made according to the process of claim 1.

35. A nano-wire made according to the process of claim 1.

36. A nano-crystal made according to the process of claim 31.

37. An artificial atom made according to the process of claim 1.

* * * * *